Aug. 10, 1965 E. S. BOERNER Plant Pat. 2,547
CHRYSANTHEMUM PLANT
Filed April 29, 1964
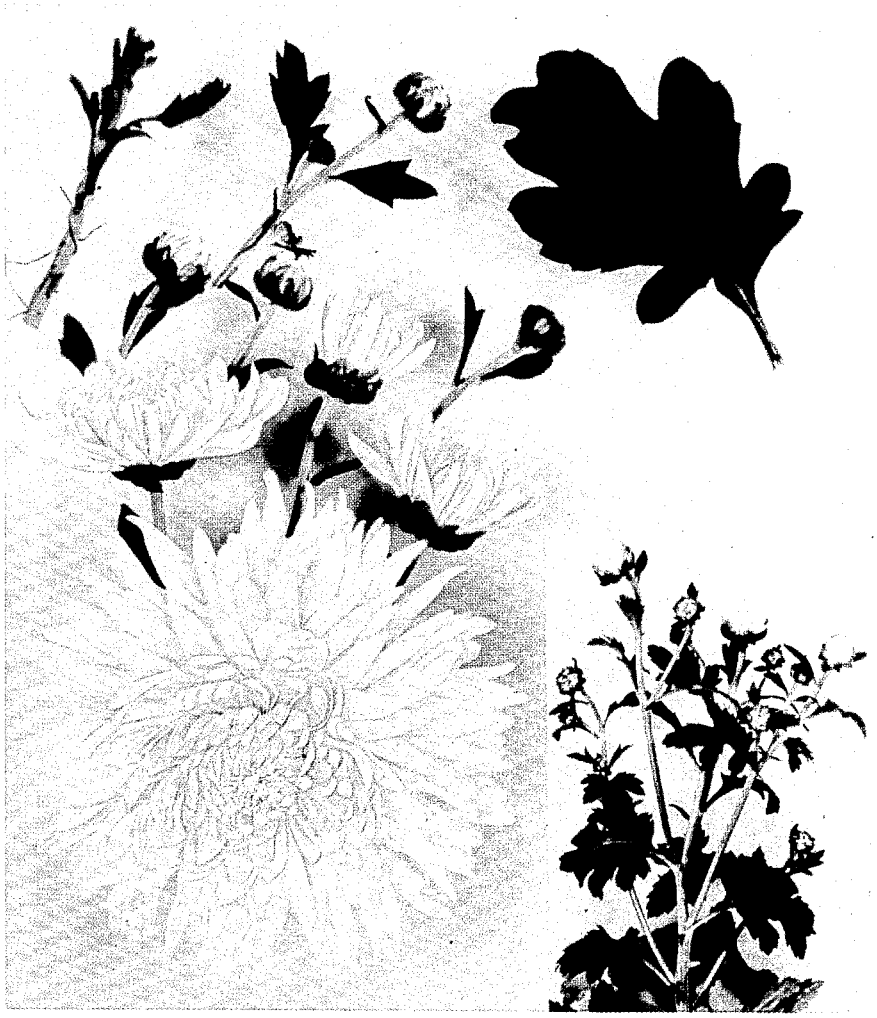
Inventor.
E. S. Boerner
By: Robb & Robb
Attorneys.

United States Patent Office

Plant Pat. 2,547
Patented Aug. 10, 1965

2,547
CHRYSANTHEMUM PLANT

Eugene S. Boerner, Newark, N.Y., assignor to Jackson & Perkins Company, Newark, N.Y., a corporation of New York Filed Apr. 29, 1964, Ser. No. 363,688
1 Claim. (Cl. Plt.—77)

The present invention relates to a new and distinct variety of chrysanthemum plant of the decorative type with incurved center, which was originated by me by crossing the variety known as "Golden Sceptre" (unpatented) with the variety known as "Golden Cockatoo" (Plant Patent No. 1638).

The primary objective of this breeding was to produce a new chrysanthemum variety having the strength, hardiness and earliness of the parent variety "Golden Cockatoo," combined with a flower size and type corresponding to the parent variety "Golden Sceptre." This objective was fully achieved, along with other desirable improvements, as evidenced by the following unique combination of characteristics which are outstanding in the new variety and distinguish it from its parents, as well as from all other varieties of which I am aware:

(1) Vigorous, strong, upright and free habits of growth;
(2) An early blooming habit ranging from about the end of September and continuing until freezing weather in Northern New York State;
(3) Good floriferousness;
(4) Large flower size and good flower thickness; and
(5) A distinctive and attractive white general color tonality, with the center of the flower being Picric Yellow.

Asexual reproduction of the new variety by both top cuttings and underground runners, as performed at Newark, New York, shows that the foreging characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen stem which is depicted in black and white for the purpose of illustrating the form and habit of growth of the plant.

The following is a detailed description of the new variety, with color terminology in accordance with Ridgway's Color Standards and Nomenclature, as based upon observatioins of specimens grown outdoors at Newark, New York, during the early morning in the first part of the month of October:

Parentage: Seedling.
*Seed parent.*—"Golden Sceptre."
*Pollen parent.*—"Golden Cockatoo."

Classification: Decorative; incurved center.
Growth: Vigorous.
Cold resistance: Winter hardy in northern New York State.
Blooming period: In Newark, New York, climatic area, blooming starts about end of September and continues until freezing weather.

*Flower*

Bud:
*Color.*—When petals first divide—Light Green-Yellow, Plate 5. When petals begin to unfurl—Pale Lemon - Yellow, Plate 4. When half-blown—inside: Marguerite Yellow, Plate 30, lightly overcast with Picric Yellow, Plate 4; outside: White, Plate 53, lightly overcast with Pinard Yellow, Plate 4.
*Peduncle.*—Color—Light Grape Green, Plate 41. Strength—Strong.

Bloom:
*Size.*—5½ inches.
*Stem.*—Strong.
*Form.*—Decorative; incurved center; 3 inches thick.
*Petalage.*—Very double.
*Color.*—Center of flower—Picric Yellow, Plate 4. Outer petals—White, Plate 53. Base of petals—Light Viridine Yellow, Plate 5. Inside of petals—White, Plate 53. Reverse of petals—White, Plate 53.
*Petals.*—Texture—Thick. Form—Oval.
*Fragrance.*—Characteristic chrysanthemum.

*Plant*

Form: Upright; branching.
Growth: Vigorous and free; full of bloom.
Foliage:
*Size.*—Medium.
*Quantity.*—Normal.
*Color.*—Upper side—Dark Cress Green, Plate 31. Rerverse side—Light Hellebore Green, Plate 17.
*Texture.*—Leathery.

I claim:

A new and distinct variety of chrysanthemum plant of the decorative class, substantially as herein shown and described, characterized particularly as to novelty by the unique combination of vigorous, strong, upright and free habits of growth, an early blooming habit ranging from about the end of September and continuing until freezing weather in northern New York State, good floriferousness, large flower size and good flower thickness, and a distinctive and attractive White general color tonality, with the center of the flower being Picric Yellow.

No reference cited.

ABRAHAM G. STONE, *Primary Examiner.*